United States Patent [19]

Kauffman et al.

[11] 4,448,887
[45] May 15, 1984

[54] METHOD FOR THE PARTICLE SIZE INDEPENDENT SPECTROMETRIC DETERMINATION OF METAL PARTICLES IN LUBRICATING OILS AND HYDRAULIC FLUIDS

[75] Inventors: Robert E. Kauffman, Kettering; Wendell E. Rhine, Dayton; Costandy S. Saba, Springfield, all of Ohio

[73] Assignee: The United States of America as represented by the Secretary of the Air Force, Washington, D.C.

[21] Appl. No.: 429,939

[22] Filed: Sep. 30, 1982

[51] Int. Cl.³ .................... G01N 21/71; G01N 33/20; G01N 33/28
[52] U.S. Cl. ........................... 436/60; 73/64; 356/70; 436/73; 436/175
[58] Field of Search ................... 436/60, 73, 153, 154, 436/171, 175; 73/64; 356/36, 70

[56] References Cited

U.S. PATENT DOCUMENTS

| | | | |
|---|---|---|---|
| 2,818,766 | 1/1958 | Huchinson | 356/36 |
| 3,580,704 | 5/1971 | Pickup et al. | 436/60 X |
| 3,942,360 | 3/1976 | Wada | 73/61 R |
| 3,981,584 | 9/1976 | Guymer | 356/70 |
| 4,176,545 | 12/1979 | Oddo | 73/64 |
| 4,324,758 | 4/1982 | Eisentraut et al. | 422/61 |

OTHER PUBLICATIONS

W. W. Seifert et al., "A Method for the Study of Wear Particles in Lubricating Oils", *Wear* 1972, 21, 27–42.
V. C. Westcoff et al., "Investigation of Iron Content of Lubricating Oil Using a Ferrograph & an Emission Spectrometer", *Wear* 1973, 23, 239–249.
J. R. Brown et al., "Particle Size Independent Spectrometric Determination of Wear Metals in Aircraft Lubricating Oils", *Analytical Chemistry*, 1980, 52, 2365–2370.
C. S. Saba et al., "Efficiencies of Sample Introduction Systems for the Transport of Metallic Particles in Plasma Emission & Atomic Absorption Spectrometry", *Analytical Chemistry* 1981, 53, 1099–1103.
R. E. Kauffman et al., "Quantitative Multielement Determination of Metallic Wear Species in Lubricating Oils and Hydraulic Fluids", *Analytical Chemistry* 1982, 54, 975–979.

*Primary Examiner*—Arnold Turk
*Assistant Examiner*—Robert J. Hill, Jr.
*Attorney, Agent, or Firm*—Donald J. Singer; Charles E. Bricker

[57] ABSTRACT

The degree of wear metal contamination in an oil is determined by treating a sample of the oil with a mixture of HF/HCl/nitric acid, diluting the oil/acid mixture with a solvent mixture consisting of a nonionic surfactant and a diluent, and spectrometrically analyzing the resulting diluted mixture. Severe wear in an oil wetted apparatus may be detected by directly analyzing spectrometrically a sample of the oil and comparing the results of such analysis with the results obtained according to the acid dissolution method described above.

20 Claims, 1 Drawing Figure

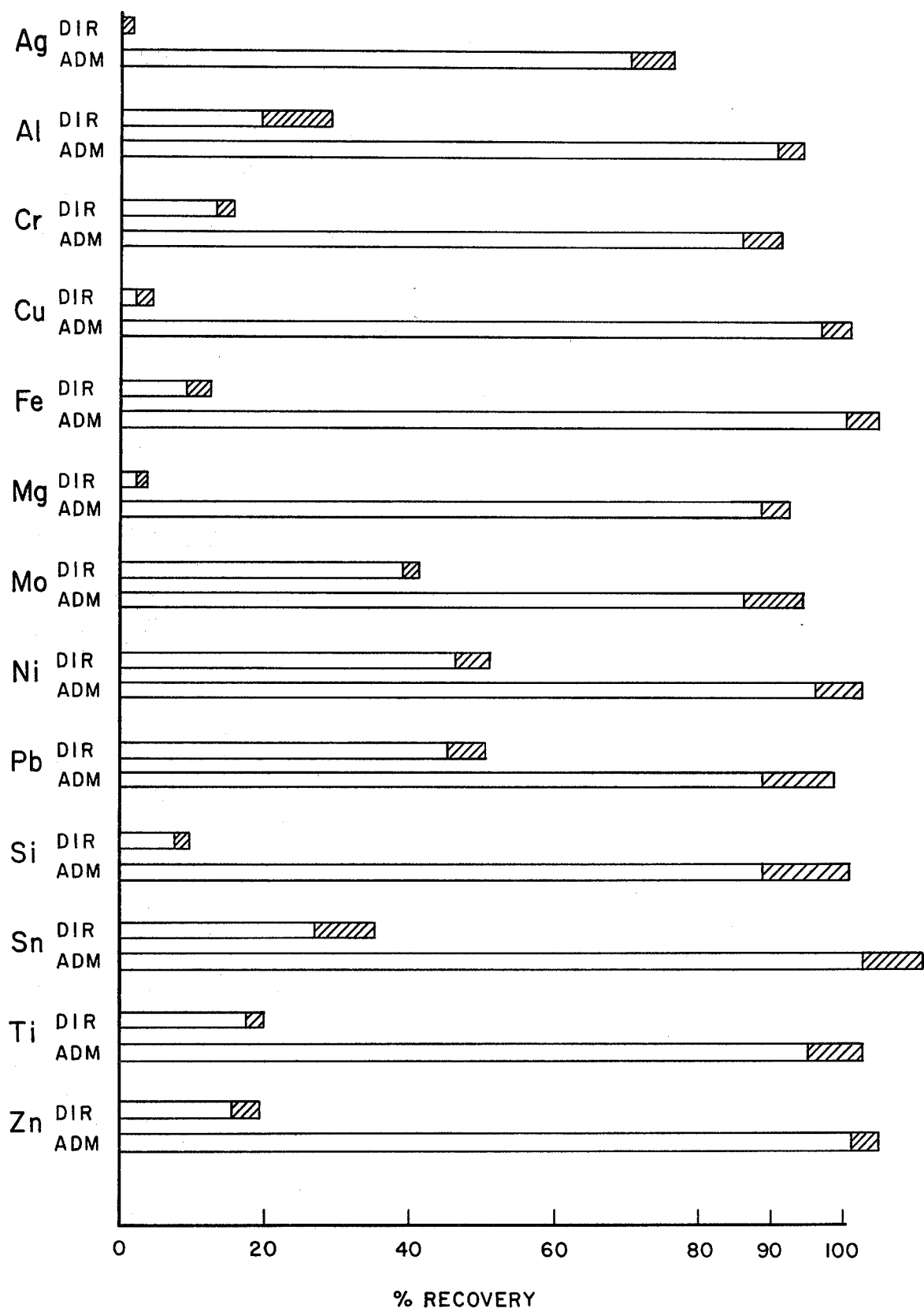

METHOD FOR THE PARTICLE SIZE INDEPENDENT SPECTROMETRIC DETERMINATION OF METAL PARTICLES IN LUBRICATING OILS AND HYDRAULIC FLUIDS

RIGHTS OF THE GOVERNMENT

The invention described herein may be manufactured and used by or for the Government of the United States for all governmental purposes without the payment of any royalty.

BACKGROUND OF THE INVENTION

This invention relates to a method for determining the degree of contamination of liquids, particularly the level of metal contaminants in liquids such as hydraulic fluids and lubricating oil.

Wear at the interface between moving parts is a normal characteristic of machine operation. The kind and the rate of wear depend on the machine. Lubrication is normally provided between moving surfaces to minimize the wear. During operation millions of minute wear particles, ranging in size from submicron to 100 $\mu m$ or larger, enter the lubricating oil.

It has been long recognized that a knowledge of the quantity and of the rate of increase in the quantity of contaminants in a lubricating oil or hydraulic fluid can give valuable insight into the condition of the machine. Because the quantity of such material is extremely small in a machine in good condition, it has been necessary to employ sophisticated techniques to analyze the oil or fluid.

Atomic absorption spectrophotometric (AAS) and atomic emission spectrometric (AES) techniques have been used for the determination of wear metals in used lubricating oils. Although spectrometers perform a rapid analysis of wear metal particles, the accuracy of the analysis is particle-size dependent. To enable the spectrometers to perform particle size independent analyses, ensuring accurate component wear evaluations, procedures have been developed which incorporate acid dissolution of the metal particles before spectrometric analysis. The most useful of such procedures is a rapid, multielement particle size independent method (PSIM) which is effective for Al, Cu, Fe, Mg, Mo, Ni, Sn and Ti in synthetic ester base lubricating oils (Brown, J. R., Saba, C. S., Rhine, W. E. and Eisentraut, K. J., Analytical Chemistry, 1980, 52, 2365).

The present invention provides an improved particle size independent method for determining the degree of metal wear contamination of liquids. The method of this invention is applicable to all liquid lubricants or hydraulic fluids, the recoveries of Al, Cr, Cu, Fe, Mg, Mo, Ni, Pb, Si, Sn, Ti and Zn are quantitative and recoveries for Ag, Cd and Na are greatly improved, and the reaction time and temperature are considerably reduced.

Accordingly, it is an object of the present invention to provide an improved method for determining the degree of wear metal contamination of liquids.

Other objects, aspects and advantages of the present invention will become apparent to those skilled in the art from a reading of the following detailed disclosure.

SUMMARY OF THE INVENTION

In accordance with the present invention there is provided a method for determining the degree of wear metal contamination of liquids such as oil utilized in hydraulic systems, lubricating oil or the like, which comprises combining a sample of the oil with a quantity of a mixture of acids, heating the mixture to dissolve the wear metal particles, diluting the oil/acid mixture with a solvent mixture, and analyzing the diluted mixture spectrometrically to determine the quantity of wear metal in the sample.

Also provided in accordance with the invention is a method for detecting severe wear at an early stage which comprises analyzing a first sample of an oil as described above to determine the total quantity of wear metal in the sample, spectrometrically analyzing a second sample of the oil directly, i.e., without dissolving the wear metal particles in the acid mixture, and comparing the results of these two analyses to determine the quantity of large wear metal particles.

BRIEF DESCRIPTION OF THE DRAWING

The FIGURE is a graph showing the percent recoveries of 13 metals in a simulated used lubricating oil determined by direct spectrometric analysis (DIR) and by the method of this invention (ADM).

DESCRIPTION OF THE PREFERRED EMBODIMENT

The method of this invention is feasible for ascertaining the condition of equipment or apparatus wherein lubricated moving metal parts are involved including, for example, jet engines, reciprocating engines, industrial machinery, hydraulic systems, and the like, from which representative samples of lubricating oil or hydraulic fluid can be taken. The method of this invention can be used with liquid hydrocarbon oils derived from crude petroleum, and synthetic oils including, for example, ester oils, silicones and polyglycols.

The acid mixture employed in the method of this invention consists of about 8 to 12 percent (w/w) of 48% ACS reagent grade hydrofluoric acid, about 76 to 84 percent (w/w) of 37% ACS reagent grade hydrochloric acid and about 8 to 12 percent (w/w) of 70% ACS reagent grade nitric acid. This acid mixture is conveniently prepared by slowly adding the concentrated hydrofluoric acid to the concentrated nitric acid, with mixing, and thereafter slowly adding the concentrated hydrochloric acid to the hydrofluoric/nitric acid mixture, again with mixing. The resulting mixture should be allowed to stand until offgassing, if any, is complete, prior to using the acid mixture.

The solvent mixture employed in the method of this invention consists of about 20 to 40 parts by weight of a nonionic surfactant and about 60 to 80 parts by weight of a diluent. A presently preferred group of nonionic surfactants have the general formula $RO(CH_2CH_2O)_nH$, wherein R is a linear alkyl group having 9 to 11 carbon atoms and n is a number having a value of about 1 to 10. A mixture of these surfactants wherein R has an average of 10 carbon atoms and n has an average value of 6 is available commercially from Shell Chemical Co., One Shell Plaza, Houston, Tex., under the tradename Neodol 91-6. The diluent is any material which is a solvent for the oil being tested and which will not interfere with the analysis. Suitable diluents include kerosene and methyl isobutyl ketone (MIBK). Presently preferred solvent mixtures are (a) 25 parts Neodol 91-6 and 75 parts MIBK, and (b) 35 parts Neodol 91-6 and 65 parts kerosene.

In order to calibrate the spectrometric apparatus it is necessary to prepare a series of blanks and standards.

Due to the high concentration and the variety of metal-containing additives employed in lubricating oils, it is important that an unused oil of the identical type and name brand, preferably of the same lot and batch, be used to prepare the standards and blanks for the analysis of used oils. Errors will occur if the oil used for the standard and the blank is different from that of the used sample. Such errors can be larger than the content of wear metals in the used oil sample. The spectrometric standards may conveniently be prepared by diluting a multielement concentrate with the appropriate base oil.

Organometallic single-element alkyl aryl sulfonate concentrates are available under the tradename Conostan from the Conostan Division, Continental Oil Co., Ponca City, OK. These concentrates may be diluted with an amount of oil, such as, for example, 85 hydrocarbon base oil, to obtain single-element, high concentration standards, e.g., 900 ppm. The single element standards may be mixed to provide multielement concentrates, which can then be further diluted to desired concentrations with an unused oil of the type being analyzed.

The spectrometric apparatus employed in the method of this invention may be a flame atomic absorption spectrophotometer (AAS), an inductively coupled plasma (ICP) emission spectrometer, a direct current plasma (DCP) emission spectrometer, or other suitable apparatus. Regardless of the type of apparatus, it is desirable that an acid resistant sample introduction system be employed therewith.

In carrying out the method of this invention, the used oil sample is first mixed with the above-described acid mixture in a ratio ranging from 4:1 to 6:1, preferably 5:1, by weight. The mixture of oil and acid is agitated continuously for about 5 minutes at a temperature in the approximate range of 20° to 70° C. In order that the method of this invention be independent of the type of the base oil, it is presently preferred that a temperature of 40°±5° C. be used when using ultrasonic agitation and 25°±5° C. when using a vortex mixer. If molybdenum is found or known to be in the oil sample a reaction temperature of 65°±5° C. with ultrasonic agitation is required for total recovery of the Mo.

The reaction mixture is cooled and then diluted with the above-described solvent mixture in a weight ratio of 1:2 or greater, preferably 1:4, by weight. The container is capped, then agitated until the acid/oil mixture is thoroughly homogenized. The sample is then ready for spectrometric analysis.

The spectrometric standards and blanks are made ready for analysis using the above-described procedure.

The following examples illustrate the invention.

EXAMPLE I

Preparation of Reagents

A mixture of HF/HCl/HNO$_3$ (1:8:1) was prepared by slowly adding 10 g of 48% ACS reagent grade HF to 10 g of 70% ACS reagent grade HNO$_3$ in a polyethylene bottle. To this acid mixture 80 g of 37% ACS reagent grade HCl was slowly added with thorough mixing. The bottle containing the acid mixture was loosely capped and placed in a fume hood until evolution of the reddish brown gas ceased (about 24 hours).

The following solvent mixtures were prepared:

(a) a mixture of 10 g of methyl isobutyl ketone (MIBK) and 90 g of isopropyl alcohol (IPA), hereinafter referred to as MIBK/IPA.

(b) a mixture of 25 g of Neodol 91-6 and 75 g of MIBK, hereinafter referred to as Neodol/MIBK.

(c) a mixture of 35 g of Neodol 91-6 and 65 g of kerosene, hereinafter referred to as Neodol/kerosene.

12- and 20-element standards were prepared with concentrations of 100, 75, 50, 30 and 6 ppm by diluting their respective 900 ppm Conostan concentrates (in 85 hydrocarbon base oil) with the appropriate amounts of MIL-L-7808H ester oil, 245 hydrocarbon base oil or MIL-H-5606 hydraulic fluid.

EXAMPLE II

Evaluation of Solvent Systems 20 g of each standard was diluted with 4 g of HF/HCl/HNO (1:8:1) and 116 g of MIBK/IPA, Neodol/MIBK or Neodol/kerosene. The stability of the standards was determined by comparing freshly prepared, diluted standards with diluted standards which had been aged for 3 days, 1 week, 2 weeks and 1 month. The Conostan standards were stable for 1-2 weeks using the solvent systems containing the Neodol 91-6, but were stable for less than 1 week when isopropyl alcohol was used as the homogenizing agent.

EXAMPLE III

Analysis of Metal Powder Suspensions 100 ppm simulated wear metal suspensions were prepared with 325 mesh (<44 μm) or 200 mesh (<74 μm) metal powders by directly weighing 13 metal powders (Ag, Al, Cr, Cu, Fe, Mg, Mo, Ni, Pb, Sn, Si, Ti and Zn) into a polyethylene bottle and diluting with ester oil or hydraulic fluid. The two metal powder suspensions, one in ester oil and the other in hydraulic fluid, were analyzed directly on a DCP spectrometer and according to the acid dissolution method (ADM) of this invention. The results of these tests are shown in the sole FIGURE. The percent recoveries shown are the averages determined from triplicate analyses of the two suspensions.

The percent recoveries ranged from 2 to 48 percent when analyzed directly without acid (DIR) and 89 to 102% when analyzed by the acid dissolution method (ADM), except for Ag, indicating that the larger particles in suspension can only be analyzed using acid dissolution. The recovery of Ag was less than 1% when analyzed directly, but by the acid dissolution method (ADM) recovery was about 75%, thus illustrating the usefulness of the ADM even for Ag.

The relative standard deviations (shaded area) ranged from 2 to 12% for all samples analyzed by the ADM.

Various modifications may be made by those skilled in the art within the scope of the following claims without departing from the spirit thereof.

We claim:

1. A method for determining the degree of wear metal contamination of an oil which comprises the steps of:

(a) combining a sample of said oil with an acid mixture consisting of about 8 to 12 weight percent of concentrated HF, about 76 to 84 weight percent of concentrated HCl and about 8 to 12 weight percent of concentrated nitric acid;

(b) heating the resulting oil/acid mixture to dissolve wear metal particles;

(c) diluting said oil/acid mixture with a solvent mixture consisting of about 20 to 40 parts by weight of a nonionic surfactant and about 60 to 80 parts of a diluent; and (d) spectrometrically analyzing the resulting diluted mixture.

2. The method of claim 1 wherein said acid mixture consists of about 10 weight percent HF, about 80 weight percent HCl and about 10 weight percent nitric acid.

3. The method of claim 1 wherein said diluent is selected from the group consisting of kerosene and methyl isobutyl ketone.

4. The method of claim 1 wherein said surfactant has the general formula $$RO(CH_2CH_2O)_nH$$

wherein R is a linear alkyl group having 9 to 11 carbon atoms and n is a number having a value of about 1 to 10.

5. The method of claim 4 wherein R has an average of 10 carbon atoms and n has an average value of 6.

6. The method of claim 5 wherein said solvent mixture consists of 35 parts of said surfactant and 65 parts of kerosene.

7. The method of claim 5 wherein said solvent mixture consists of 25 parts of said surfactant and 75 parts of methyl isobutyl ketone.

8. The method of claim 1 wherein said oil/acid mixture is heated, with stirring, for about 5 minutes at a temperature in the approximate range of 20° to 70° C.

9. The method of claim 1 wherein said oil sample is mixed with said acid mixture in a ratio ranging from 4:1 to 6:1 by weight, and the oil/acid mixture is diluted with said solvent mixture in a ratio of at least 1:2, by weight.

10. The method of claim 9 wherein said oil:acid ratio is 5:1 and said oil/acid:solvent ratio is 1:4.

11. A method for detecting severe wear at an early stage in an oil wetted apparatus which comprises the steps of:

(a) obtaining a sample of oil from said apparatus;

(b) spectrometrically analyzing a first portion of said sample;

(c) treating a second portion of said sample with an acid mixture consisting of about 8 to 12 weight percent concentrated HF, about 76 to 84 weight percent concentrated HCl and about 8 to 12 weight percent concentrated nitric acid;

(d) heating the resulting oil/acid mixture to dissolve wear metal particles;

(e) diluting said oil/acid mixture with a solvent mixture consisting of about 20 to 40 parts by weight of a nonionic surfactant and about 60 to 80 parts of a diluent;

(f) spectrometrically analyzing the resulting diluted mixture; and (g) comparing the results obtained according to step (b) with the results obtained according to step (f).

12. The method of claim 11 wherein said acid mixture consists of about 10 weight percent HF, about 80 weight percent HCl and about 10 weight percent nitric acid.

13. The method of claim 11 wherein said diluent is selected from the group consisting of kerosene and methyl isobutyl ketone.

14. The method of claim 11 wherein said surfactant has the general formula $$RO(CH_2CH_2O)_nH$$

wherein R is a linear alkyl group having 9 to 11 carbon atoms and n is a number having a value of about 1 to 10.

15. The method of claim 14 wherein R has an average of 10 carbon atoms and n has an average value of 6.

16. The method of claim 15 wherein said solvent mixture consists of 35 parts of said surfactant and 65 parts of kerosene.

17. The method of claim 15 wherein said solvent mixture consists of 25 parts of said surfactant and 75 parts of methyl isobutyl ketone.

18. The method of claim 11 wherein said acid/oil mixture is heated, with stirring, for about 5 minutes at a temperature in the approximate range of 20° to 70° C.

19. The method of claim 11 wherein said second portion is mixed with said acid mixture in a ratio ranging from 4:1 to 6:1, by weight, and the oil/acid mixture is diluted with said solvent mixture in a ratio of at least 1:2, by weight.

20. The method of claim 19 wherein said oil:acid ratio is 5:1 and said oil/acid:solvent ratio is 1:4.

* * * * *